(12) United States Patent
Lerestif et al.

(10) Patent No.: US 7,867,994 B2
(45) Date of Patent: *Jan. 11, 2011

(54) PROCESS FOR THE SYNTHESIS OF IVABRADINE AND ADDITION SALTS THEREOF WITH A PHARMACEUTICALLY ACCEPTABLE ACID

(75) Inventors: Jean-Michel Lerestif, Yvetot (FR);
Jean-Pierre Lecouve, Le Havre (FR);
Jean-Claude Souvie, Le Havre (FR);
Daniel Brigot, Sainte-Marie-des-Champs (FR);
Stephane Horvath, La-Chapelle-Saint-Mesmin (FR);
Marie-Noelle Auguste, Orleans (FR);
Gerard Damien, Meung-sur-Loire (FR)

(73) Assignee: Les Laboratoires Servier, Suresnes Cedex (FR)

( * ) Notice: Subject to any disclaimer, the term of this patent is extended or adjusted under 35 U.S.C. 154(b) by 765 days.

This patent is subject to a terminal disclaimer.

(21) Appl. No.: 11/654,719

(22) Filed: Jan. 18, 2007

(65) Prior Publication Data

US 2007/0135411 A1 Jun. 14, 2007

Related U.S. Application Data

(63) Continuation of application No. 11/057,492, filed on Feb. 14, 2005, now Pat. No. 7,176,197.

(30) Foreign Application Priority Data

Apr. 13, 2004 (FR) .................................. 04 03830

(51) Int. Cl.
*C07D 223/16* (2006.01)
*C07D 405/06* (2006.01)
*A61K 31/55* (2006.01)
*A61P 9/00* (2006.01)

(52) U.S. Cl. .................................. 514/212.07; 540/523

(58) Field of Classification Search ............ 514/212.07; 540/523

See application file for complete search history.

(56) References Cited

U.S. PATENT DOCUMENTS

| 4,584,293 A | 4/1986 | Reiffen et al. |
| 4,737,495 A | 4/1988 | Bomhard et al. |
| 5,296,482 A | 3/1994 | Peglion et al. |

FOREIGN PATENT DOCUMENTS

| EP | 0534859 | 3/2003 |
| GB | 2099425 | 12/1982 |
| SU | 1160935 | 6/1985 |

OTHER PUBLICATIONS

*Eurasian Search Report* for Eurasian Application No. 200500238, Jun. 6, 2005.
*International Search Report* for International Application No. PCT/FR2005/000394, Jun. 30, 2005.
Sorbera, et al., *Drugs of the Future*, 2003, 28, 652-658.

*Primary Examiner*—Bruck Kifle
(74) *Attorney, Agent, or Firm*—Hueschen and Sage

(57) ABSTRACT

Process for the synthesis of ivabradine of formula (I):

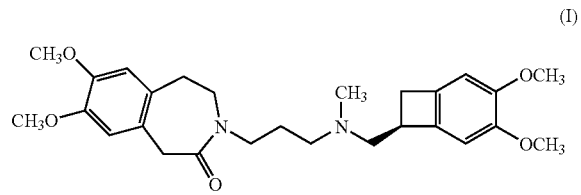

addition salts thereof with a pharmaceutically acceptable acid and hydrates thereof.

α crystalline form of ivabradine hydrochloride.

Medicinal products containing α crystalline form of ivabradine hydrochloride, which are useful as bradycardics.

17 Claims, No Drawings

PROCESS FOR THE SYNTHESIS OF IVABRADINE AND ADDITION SALTS THEREOF WITH A PHARMACEUTICALLY ACCEPTABLE ACID

The present invention relates to a process for the industrial synthesis of ivabradine of formula (I):

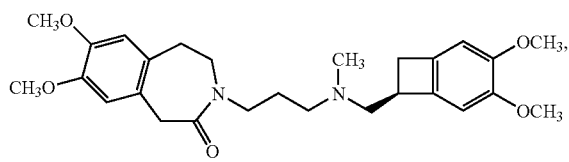

(I)

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, addition salts thereof with a pharmaceutically acceptable acid and hydrates thereof.

BACKGROUND OF THE INVENTION

Ivabradine, and addition salts thereof with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also of various pathologies involving rhythm disturbances, especially supraventricular rhythm disturbances, and in the treatment of heart failure.

DESCRIPTION OF THE PRIOR ART

The preparation and therapeutic use of ivabradine and addition salts thereof with a pharmaceutically acceptable acid, and more especially its hydrochloride, have been described in the European patent specification EP 0 534 859.

That patent specification describes the synthesis of ivabradine hydrochloride by reacting the compound of formula (II):

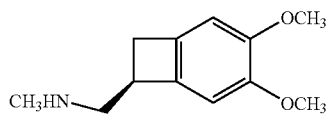

(II)

with the compound of formula (III):

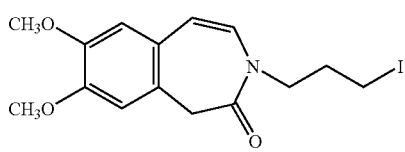

(III)

to yield the compound of formula (IV):

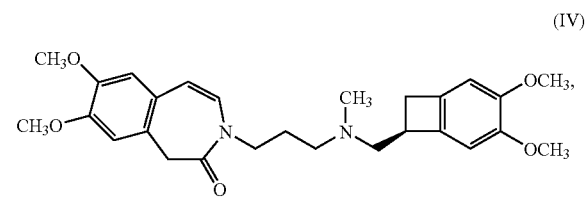

(IV)

the catalytic hydrogenation of which results in ivabradine, which is then converted into its hydrochloride.

That method has the disadvantage of yielding ivabradine hydrochloride in only a very low yield—less than 17% over the 3 steps as a whole.

In view of the pharmaceutical value of ivabradine and its salts, and more especially its hydrochloride, it has been important to be able to obtain it by an effective industrial synthesis process comprising a minimal number of steps and allowing ivabradine and its salts, and more especially its hydrochloride, to be obtained in a satisfactory yield.

DETAILED DESCRIPTION OF THE INVENTION

The Applicant has now developed a synthesis process allowing ivabradine salts to be obtained in a single step starting from a salt of the compound of formula (II), in a very good yield.

More specifically, the present invention relates to a process for the synthesis of ivabradine of formula (I), addition salts thereof with a pharmaceutically acceptable acid, and hydrates thereof, characterised in that the compound of formula (V)

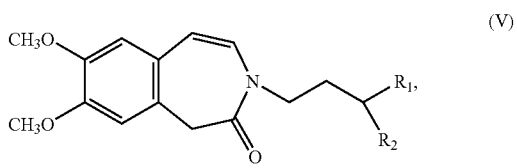

(V)

wherein $R_1$ and $R_2$, which may be the same or different, each represent a linear or branched $(C_1\text{-}C_8)$alkoxy group or form, together with the carbon atom carrying them, a 1,3-dioxane, 1,3-dioxolane or 1,3-dioxepane ring, is subjected to a catalytic hydrogenation reaction, and then the compound of formula (VI) thereby obtained:

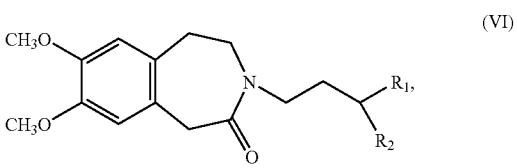

(VI)

wherein $R_1$ and $R_2$ are as defined hereinbefore, is subjected to a reaction with the compound of formula (VII):

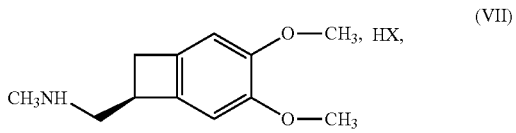
(VII)

wherein HX represents a pharmaceutically acceptable acid, in the presence of hydrogen and a catalyst, to yield directly, after filtering off the catalyst and isolation, the addition salt of ivabradine with the acid HX, which is optionally subjected, when it desired to obtain free ivabradine, to the action of a base.

Among the pharmaceutically acceptable acids, there may be mentioned by way of non-limiting example hydrochloric, hydrobromic, sulphuric, phosphoric, acetic, trifluoroacetic, lactic, pyruvic, malonic, succinic, glutaric, fumaric, tartaric, maleic, nitric, citric, ascorbic, oxalic, methanesulphonic, benzenesulphonic and camphoric acids.

This process makes it possible for addition salts of ivabradine, and especially its hydrochloride, to be obtained directly in a single step starting from the corresponding salt of the amine of formula (II), with excellent purity and in a very good yield.

Among the catalysts which can be used in the hydrogenation reaction of the compound of formula (V), there may be mentioned, without implying any limitation, palladium, platinum, nickel, ruthenium, rhodium, and their compounds, particularly in supported form or in oxide form.

The catalyst for the hydrogenation reaction of the compound of formula (V) is preferably palladium-on-carbon.

The temperature of the hydrogenation reaction of the compound of formula (V) is preferably from 20 to 100° C., more preferably from 40 to 80° C., even more preferably from 45 to 65° C.

The hydrogen pressure during the hydrogenation reaction of the compound of formula (V) is preferably from 1 to 220 bars, more preferably from 1 to 100 bars, even more preferably from 1 to 30 bars.

The hydrogenation reaction of the compound of formula (V) is preferably carried out in a non-acidic solvent.

Among the preferred non-acidic solvents which can be used in the hydrogenation reaction of the compound of formula (V), there may be mentioned, without implying any limitation, acetates, alcohols, preferably ethanol, methanol or isopropanol, tetrahydrofurane, toluene, dichloromethane and xylene.

Advantageously, the intermediate compound of formula (VI) is not isolated and the crude reaction product is used as such in the reductive amination reaction.

Among the catalysts which can be used in the reductive amination reaction between the compound of formula (VI) and the compound of formula (VII), there may be mentioned, without implying any limitation, palladium, platinum, nickel, ruthenium, rhodium, and their compounds, particularly in supported form or in oxide form.

The catalyst for the reductive amination reaction between the compound of formula (VI) and the compound of formula (VII) is preferably palladium-on-carbon.

The temperature of the reductive amination reaction between the compound of formula (VI) and the compound of formula (VII) is preferably from 30 to 120° C., more preferably from 40 to 100° C., even more preferably from 60 to 95° C.

The hydrogen pressure during the reductive amination reaction between the compound of formula (VI) and the compound of formula (VII) is preferably from 1 to 220 bars, more preferably from 1 to 100 bars, even more preferably from 10 to 60 bars.

In the process according to the invention, the compounds of formulae (V) and (VI) that are preferably used are the compounds of formulae (Va) and (VIa), particular cases of the compounds of formulae (V) and (VI) wherein $R_1$ and $R_2$ form, together with the carbon atom carrying them, a 1,3-dioxane, 1,3-dioxolane or 1,3-dioxepane ring.

The compounds of formulae (Va), a particular case of the compounds of formula (V) wherein $R_1$ and $R_2$ form, together with the carbon atom carrying them, a 1,3-dioxane, 1,3-dioxolane or 1,3-dioxepane ring, and also the compounds of formula (VI), are new products which are useful as synthesis intermediates in the chemical or pharmaceutical industry, especially in the synthesis of ivabradine and addition salts thereof with a pharmaceutically acceptable acid, and as such they form an integral part of the present invention.

A process which is preferred according to the invention is the process that uses, as synthesis intermediate, the compound of formula (VIIa), a particular case of the compounds of formula (VII) wherein HX represents hydrochloric acid, thereby yielding ivabradine hydrochloride of formula (Ia).

In that case, the process according to the present invention yields ivabradine hydrochloride in α crystalline form—the α form—which is well defined and perfectly reproducible and which especially has valuable characteristics in terms of filtration, drying, stability and ease of formulation.

That α crystalline form is new and constitutes another aspect of the present invention.

The α crystalline form of ivabradine hydrochloride is characterised by the following powder X-ray diffraction diagram measured using a PANalytical X'Pert Pro diffractometer together with an X'Celerator detector and expressed in terms of ray position (Bragg's angle 2 theta, expressed in degrees), ray height (expressed in counts), ray area (expressed in counts×degrees), ray width at half-height ("FWHM", expressed in degrees) and interplanar distance d (expressed in Å):

| Ray no. | Angle 2 theta (degrees) | Height (counts) | Area (counts × degrees) | FWHM (degrees) | Interplanar distance (Å) |
|---|---|---|---|---|---|
| 1 | 4.1 | 1341 | 177 | 0.1338 | 21.486 |
| 2 | 7.7 | 1266 | 146 | 0.1171 | 11.440 |
| 3 | 8.1 | 1325 | 197 | 0.1506 | 10.923 |
| 4 | 10.4 | 1630 | 161 | 0.1004 | 8.488 |
| 5 | 11.8 | 753 | 87 | 0.1171 | 7.473 |
| 6 | 12.1 | 292 | 29 | 0.1004 | 7.301 |
| 7 | 13.2 | 917 | 106 | 0.1171 | 6.709 |
| 8 | 13.8 | 875 | 130 | 0.1506 | 6.423 |
| 9 | 15.3 | 281 | 37 | 0.1338 | 5.790 |
| 10 | 16.2 | 816 | 108 | 0.1338 | 5.478 |
| 11 | 16.5 | 2784 | 459 | 0.1673 | 5.381 |
| 12 | 17.4 | 1308 | 129 | 0.1004 | 5.106 |
| 13 | 18.1 | 455 | 52 | 0.1171 | 4.885 |
| 14 | 19.4 | 223 | 37 | 0.1673 | 4.569 |
| 15 | 20.2 | 3282 | 487 | 0.1506 | 4.389 |
| 16 | 20.6 | 305 | 45 | 0.1506 | 4.310 |
| 17 | 21.3 | 550 | 91 | 0.1673 | 4.165 |
| 18 | 21.9 | 1266 | 230 | 0.184 | 4.050 |
| 19 | 22.4 | 416 | 41 | 0.1004 | 3.972 |
| 20 | 23.0 | 262 | 35 | 0.1338 | 3.861 |

-continued

| Ray no. | Angle 2 theta (degrees) | Height (counts) | Area (counts × degrees) | FWHM (degrees) | Interplanar distance (Å) |
|---|---|---|---|---|---|
| 21 | 23.3 | 184 | 27 | 0.1506 | 3.814 |
| 22 | 24.4 | 309 | 51 | 0.1673 | 3.651 |
| 23 | 25.0 | 362 | 72 | 0.2007 | 3.566 |
| 24 | 25.7 | 1076 | 142 | 0.1338 | 3.459 |
| 25 | 26.5 | 2925 | 579 | 0.2007 | 3.363 |
| 26 | 26.8 | 821 | 135 | 0.1673 | 3.325 |
| 27 | 27.8 | 488 | 97 | 0.2007 | 3.212 |
| 28 | 28.4 | 620 | 123 | 0.2007 | 3.142 |
| 29 | 29.2 | 428 | 56 | 0.1338 | 3.057 |

The crystalline form may also be evaluated by other processes typical in the art, not limited to Ramen spectroscopy and infra red spectroscopy.

The invention relates also to pharmaceutical compositions comprising as active ingredient the α crystalline form of ivabradine hydrochloride together with one or more appropriate, inert and non-toxic excipients. Among the pharmaceutical compositions according to the invention there may be mentioned, more especially, those that are suitable for oral, parental (intravenous or subcutaneous) or nasal administration, tablets or dragées, sublingual tablets, capsules, lozenges, suppositories, creams, ointments, dermal gels, injectable preparations and drinkable suspensions.

The useful dosage can be varied according to the nature and severity of the disorder, the administration route and the age and weight of the patient. The dosage varies from 1 to 500 mg per day in one or more administrations.

The Examples that follow illustrate the invention.

The X-ray powder diffraction spectrum was measured under the following experimental conditions:

PANalytical X'Pert Pro diffractometer, X'Celerator detector,
voltage 45 kV, intensity 40 mA,
mounting θ-θ,
Kβ (Ni) filter,
incident-beam and diffracted-beam Soller slit: 0.04 rad,
fixed angle of divergence slits: ⅛°,
mask: 10 mm,
antiscatter slit: ¼°,
measurement mode: continuous from 3° to 30°, in increments of 0.017°,
measurement time per step: 19.7 s,
total time: 4 min 32 s,
measurement speed: 0.108°/s,
measurement temperature: ambient.

Example 1

Alpha crystalline form of 3-{3-[{[(7S)-3,4-dimethoxybicyclo-[4.2.0]octa-1,3,5-trien-7-yl]methyl}(methyl)amino]propyl}-7,8-dimethoxy-1,3,4,5-tetrahydro-2H-3-benzazepin-2-one hydrochloride Load 5.5 kg of 3-[2-(1,3-dioxolan-2-yl)ethyl]-7,8-dimethoxy-1,3-dihydro-2H-3-benzazepin-2-one, 27.5 litres of ethanol and 550 g of palladium-on-carbon into an autoclave.

Purge with nitrogen and then with hydrogen, heat to 55° C. and then hydrogenate at that temperature under a pressure of 5 bars until the theoretical amount of hydrogen has been absorbed.

Then return to ambient temperature and release the autoclave pressure.

Then add 4 kg of (7S)-3,4-dimethoxybicyclo[4.2.0]octa-1,3,5-trien-7-yl]-N-methylmethanamine hydrochloride, 11 litres of ethanol, 5.5 litres of water and 1 kg of palladium-on-carbon.

Purge with nitrogen and then with hydrogen, heat at 85° C. and then hydrogenate at that temperature under a pressure of 30 bars until the theoretical amount of hydrogen has been absorbed.

Then return to ambient temperature and purge the autoclave; then filter the reaction mixture, distil off the solvents and then isolate the ivabradine hydrochloride by crystallisation from a toluene/1-methyl-2-pyrrolidinone mixture.

Ivabradine hydrochloride is thereby obtained in a yield of 85% and with a chemical purity greater than 99%.

X-Ray Powder Diffraction Diagram:

The X-ray powder diffraction profile (diffraction angles) of the α form of ivabradine hydrochloride is given by the significant rays collated in the following table

| Ray no. | Angle 2 theta (degrees) | Height (counts) | Area (counts × degrees) | FWHM (degrees) | Interplanar distance (Å) |
|---|---|---|---|---|---|
| 1 | 4.1 | 1341 | 177 | 0.1338 | 21.486 |
| 2 | 7.7 | 1266 | 146 | 0.1171 | 11.440 |
| 3 | 8.1 | 1325 | 197 | 0.1506 | 10.923 |
| 4 | 10.4 | 1630 | 161 | 0.1004 | 8.488 |
| 5 | 11.8 | 753 | 87 | 0.1171 | 7.473 |
| 6 | 12.1 | 292 | 29 | 0.1004 | 7.301 |
| 7 | 13.2 | 917 | 106 | 0.1171 | 6.709 |
| 8 | 13.8 | 875 | 130 | 0.1506 | 6.423 |
| 9 | 15.3 | 281 | 37 | 0.1338 | 5.790 |
| 10 | 16.2 | 816 | 108 | 0.1338 | 5.478 |
| 11 | 16.5 | 2784 | 459 | 0.1673 | 5.381 |
| 12 | 17.4 | 1308 | 129 | 0.1004 | 5.106 |
| 13 | 18.1 | 455 | 52 | 0.1171 | 4.885 |
| 14 | 19.4 | 223 | 37 | 0.1673 | 4.569 |
| 15 | 20.2 | 3282 | 487 | 0.1506 | 4.389 |
| 16 | 20.6 | 305 | 45 | 0.1506 | 4.310 |
| 17 | 21.3 | 550 | 91 | 0.1673 | 4.165 |
| 18 | 21.9 | 1266 | 230 | 0.184 | 4.050 |
| 19 | 22.4 | 416 | 41 | 0.1004 | 3.972 |
| 20 | 23.0 | 262 | 35 | 0.1338 | 3.861 |
| 21 | 23.3 | 184 | 27 | 0.1506 | 3.814 |
| 22 | 24.4 | 309 | 51 | 0.1673 | 3.651 |
| 23 | 25.0 | 362 | 72 | 0.2007 | 3.566 |
| 24 | 25.7 | 1076 | 142 | 0.1338 | 3.459 |
| 25 | 26.5 | 2925 | 579 | 0.2007 | 3.363 |
| 26 | 26.8 | 821 | 135 | 0.1673 | 3.325 |
| 27 | 27.8 | 488 | 97 | 0.2007 | 3.212 |
| 28 | 28.4 | 620 | 123 | 0.2007 | 3.142 |
| 29 | 29.2 | 428 | 56 | 0.1338 | 3.057 |

Example 2

Pharmaceutical Composition

Formula for the preparation of 1000 tablets each containing 5 mg of ivabradine base:

| | |
|---|---|
| Compound of Example 1 | 5.39 g |
| Corn starch | 20 g |
| Anhydrous colloidal silica | 0.2 g |
| Mannitol | 63.91 g |
| PVP | 10 g |
| Magnesium stearate | 0.5 g |

We claim:

1. A process for the synthesis of ivabradine, 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, of formula (I):

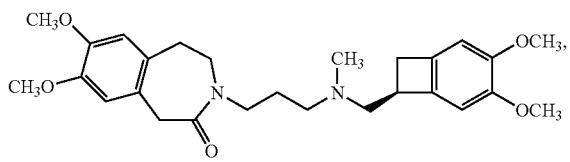

(I)

and addition salts thereof with a pharmaceutically acceptable acid,
wherein the compound of formula (V):

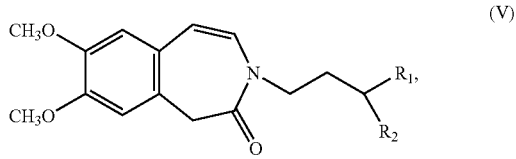

(V)

wherein $R_1$ and $R_2$, which may be the same or different, each represent linear or branched ($C_1$-$C_8$)alkoxy,
is subjected to a catalytic hydrogenation reaction,
and then the compound of formula (VI) thereby obtained:

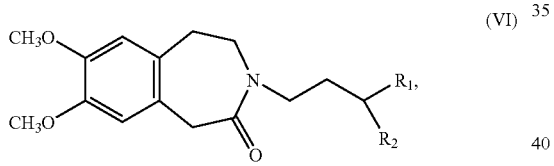

(VI)

wherein $R_1$ and $R_2$ are as defined hereinbefore,
is subjected to a reaction with the compound of formula (VII):

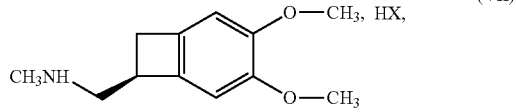

(VII)

wherein HX represents a pharmaceutically acceptable acid,
in the presence of hydrogen and a catalyst,
to yield directly, after filtering off the catalyst and isolation, the addition salt of ivabradine with the acid HX, which is optionally subjected, when it desired to obtain free ivabradine, to the action of a base.

2. The process of claim 1, wherein the catalyst for the hydrogenation reaction of the compound of formula (V) is palladium-on-carbon.

3. The process of claim 1, wherein the hydrogen pressure during the hydrogenation reaction of the compound of formula (V) is from 1 to 220 bars.

4. The process of claim 1, wherein the temperature of the hydrogenation reaction of the compound of formula (V) is from 20 to 100° C.

5. The process of claim 4, wherein the temperature of the hydrogenation reaction of the compound of formula (V) is from 40 to 80° C.

6. The process of claim 1, wherein the intermediate compound of formula (VI) is not isolated.

7. The process of claim 1, wherein the catalyst for the reaction between the compound of formula (VI) and the compound of formula (VII) is palladium-on-carbon.

8. The process of claim 1, wherein the hydrogen pressure during the reaction between the compound of formula (VI) and the compound of formula (VII) is from 1 to 220 bars.

9. The process of claim 1, wherein the temperature of the reaction between the compounds of formulae (VI) and (VII) is from 30 to 120° C.

10. The process of claim 9, wherein the temperature of the reaction between the compounds of formulae (VI) and (VII) is from 40 to 100° C.

11. The process of claim 1, wherein HX represents hydrochloric acid, thereby yielding ivabradine hydrochloride.

12. An α crystalline form of ivabradine hydrochloride of formula (Ia):

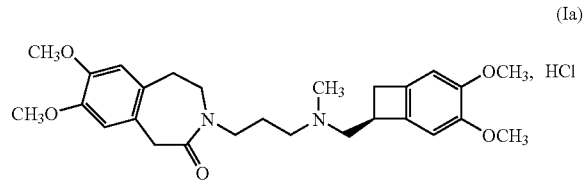

(Ia)

having a powder X-ray diffraction diagram exhibiting peaks at 10.4, 16.5, 20.2 and 26.5 deg 2 theta.

13. An α crystalline form of ivabradine hydrochloride of formula (Ia):

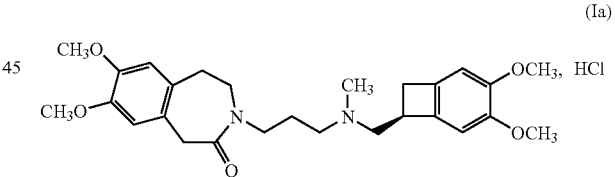

(Ia)

having a powder X-ray diffraction diagram exhibiting peaks at 4.1, 7.7, 8.1, 10.4, 16.5, 20.2 and 26.5 deg 2 theta.

14. A solid pharmaceutical composition comprising as active ingredient the α crystalline form of ivabradine hydrochloride of claim 12, in combination with one or more pharmaceutically acceptable, inert and non-toxic carriers.

15. A method of treating a living animal body afflicted with a condition selected from angina pectoris and myocardial infarct, comprising the step of administering to the living animal body an amount of the α crystalline form of ivabradine hydrochloride of claim 12 which is effective for alleviation of the condition.

16. A method of treating a living animal body afflicted with a condition selected from angina pectoris and myocardial infarct, comprising the step of administering to the living animal body an amount of the α crystalline form of ivabradine hydrochloride of claim 13 which is effective for alleviation of the condition.

17. A solid pharmaceutical composition comprising as active ingredient the α crystalline form of ivabradine hydrochloride of claim 13, in combination with one or more pharmaceutically acceptable, inert and non-toxic carriers.

* * * * *